(12) United States Patent
Schoenman

(10) Patent No.: US 8,486,059 B2
(45) Date of Patent: *Jul. 16, 2013

(54) MULTI-LAYER RETURN ELECTRODE

(75) Inventor: Arthur L. Schoenman, Longmont, CO (US)

(73) Assignee: Covidien LP, Mansfield, MA (US)

( * ) Notice: Subject to any disclaimer, the term of this patent is extended or adjusted under 35 U.S.C. 154(b) by 458 days.

This patent is subject to a terminal disclaimer.

(21) Appl. No.: 12/355,281

(22) Filed: Jan. 16, 2009

(65) Prior Publication Data

US 2009/0209953 A1     Aug. 20, 2009

Related U.S. Application Data

(60) Provisional application No. 61/029,233, filed on Feb. 15, 2008.

(51) Int. Cl.
*A61B 18/04* (2006.01)

(52) U.S. Cl.
USPC ............................................................. 606/35

(58) Field of Classification Search
USPC ......................................................... 606/32
See application file for complete search history.

(56) References Cited

U.S. PATENT DOCUMENTS

| | | | |
|---|---|---|---|
| 3,534,306 A | 10/1970 | Watrous et al. | |
| 4,895,169 A | 1/1990 | Heath | |
| 5,042,981 A * | 8/1991 | Gross | 606/32 |
| 5,061,914 A * | 10/1991 | Busch et al. | 337/140 |
| 5,797,902 A | 8/1998 | Netherly | |
| 6,053,910 A | 4/2000 | Fleenor | |
| 6,544,258 B2 | 4/2003 | Fleenor et al. | |
| 6,582,424 B2 | 6/2003 | Fleenor et al. | |
| 7,025,765 B2 | 4/2006 | Balbierz et al. | |
| 7,166,102 B2 | 1/2007 | Fleenor et al. | |
| 7,909,819 B2 * | 3/2011 | Falkenstein et al. | 606/32 |
| 2005/0085806 A1 | 4/2005 | Auge, II et al. | |
| 2006/0074411 A1 | 4/2006 | Carmel et al. | |
| 2007/0049914 A1 | 3/2007 | Eggleston | |
| 2007/0161979 A1 | 7/2007 | McPherson | |
| 2007/0244478 A1 * | 10/2007 | Bahney | 606/32 |
| 2008/0281310 A1 | 11/2008 | Dunning et al. | |
| 2008/0281311 A1 | 11/2008 | Dunning et al. | |

FOREIGN PATENT DOCUMENTS

| | | |
|---|---|---|
| CA | 1219642 | 3/1987 |
| DE | 3206947 | 9/1983 |
| DE | 3544443 | 6/1987 |
| DE | 4238263 | 5/1993 |
| DE | 4231236 | 3/1994 |
| DE | 19717411 | 11/1998 |

(Continued)

OTHER PUBLICATIONS

U.S. Appl. No. 10/609,946, filed Jun. 30, 2003.

(Continued)

*Primary Examiner* — Nicholas Lucchesi
*Assistant Examiner* — Weng Lee

(57) ABSTRACT

An electrosurgical return pad including a material backing configured to support first and second conductive materials and an insulative layer disposed therebetween. A switch element is mounted on the first conductive material and is activatable upon reaching a threshold condition, such as temperature. Upon reaching the threshold condition, the switch element automatically activates to provide electrical continuity between the first and second conductive materials to offset the threshold condition.

11 Claims, 3 Drawing Sheets

FOREIGN PATENT DOCUMENTS

| | | |
|---|---|---|
| DE | 19801173 | 7/1999 |
| DE | 10328514 | 6/2003 |
| DE | 102004010940 | 9/2005 |
| EP | 0262888 | 4/1988 |
| EP | 390937 | 10/1990 |
| EP | 836868 | 4/1998 |
| EP | 0930048 | 7/1999 |
| EP | 1051949 | 11/2000 |
| EP | 1076350 | 2/2001 |
| EP | 1468653 | 10/2004 |
| EP | 1645236 | 4/2006 |
| EP | 1707151 | 10/2006 |
| EP | 1808144 | 7/2007 |
| EP | 1902684 | 3/2008 |
| EP | 1 990 020 | 11/2008 |
| FR | 2276027 | 6/1974 |
| FR | 2516782 | 5/1983 |
| GB | 2054382 | 2/1981 |
| GB | 2374532 | 10/2002 |
| WO | WO 99/09899 | 3/1999 |
| WO | WO 00/65993 | 11/2000 |
| WO | WO 2005/087124 | 9/2005 |
| WO | WO 2005/099606 A1 | 10/2005 |
| WO | WO 2005/110263 | 11/2005 |
| WO | WO 2005/115262 | 12/2005 |
| WO | WO 2008/009385 | 1/2008 |

OTHER PUBLICATIONS

U.S. Appl. No. 11/900,190, filed Sep. 10, 2007.
U.S. Appl. No. 12/396,814, filed Mar. 3, 2009.
U.S. Appl. No. 12/395,812, filed Mar. 2, 2009.
U.S. Appl. No. 12/364,624, filed Feb. 3, 2009.
U.S. Appl. No. 12/355,281, filed Jan. 16, 2009.
U.S. Appl. No. 12/401,428, filed Mar. 10, 2009.
U.S. Appl. No. 12/407,008, filed Mar. 19, 2009.
Boyles, Walt; "Instrumentation Reference Book", 2002; Butterworth-Heinemann ; 262-264.
International Search Report EP05002027.0 dated May 12, 2005.
International Search Report EP05021944.3 dated Jan. 25, 2006.
International Search Report EP06006961 dated Aug. 3, 2006.
International Search Report EP06006961.4 dated Oct. 5, 2007.
International Search Report EP06018206.0 dated Oct. 13, 2006.
International Search Report EP06023756.7 dated Feb. 21, 2008.
International Search Report EP07000567.3 dated Dec. 3, 2008.
International Search Report EP07000885.9 dated May 15, 2007.
International Search Report EP07007783.9 dated Aug. 6, 2007.
International Search Report EP07018375.1 dated Jan. 8, 2008.
International Search Report EP07019173.9 dated Feb. 12, 2008.
International Search Report EP07019178.8 dated Feb. 12, 2008.
International Search Report EP07253835.8 dated Feb. 20, 2007.
International Search Report EP08006731.7 dated Jul. 29, 2008.
International Search Report EP08006734.1 dated Aug. 18, 2008.
International Search Report EP08006735.8 dated Jan. 8, 2009.
International Search Report EP08008510.3 dated Oct. 27, 2008.
International Search Report EP08013758.1 dated Nov. 20, 2008.
International Search Report EP08013760.7 dated Nov. 20, 2008.
International Search Report EP08155779-partial dated Sep. 8, 2008.
International Search Report EP08155779 dated Jan. 23, 2009.
International Search Report EP09152032 dated Jun. 17, 2009.
International Search Report EP09152130.2 dated Apr. 6, 2009.
International Search Report PCT/US2004/004196 dated Oct. 4, 2007.
International Search Report No. EP09152899.2 dated Jul. 1, 2009.

* cited by examiner

MULTI-LAYER RETURN ELECTRODE

CROSS-REFERENCE TO RELATED APPLICATIONS

This application claims the benefit of priority to U.S. Provisional Application Ser. No. 61/029,233 entitled "MULTI-LAYER RETURN ELECTRODE" filed Feb. 15, 2008 by Arthur Schoenman, which is incorporated by reference herein.

BACKGROUND

1. Technical Field

The present disclosure relates to electrosurgical apparatuses, systems and methods. More particularly, the present disclosure is directed to electrosurgical systems utilizing return electrodes having multi-layers.

2. Background of Related Art

Energy-based tissue treatment is well known in the art. Various types of energy (e.g., electrical, ultrasonic, microwave, cryo, heat, laser, etc.) may be applied to tissue to achieve a desired surgical result. Electrosurgery typically involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the user and applied to the tissue to be treated. The patient return electrodes are typically in the form of pads adhesively adhered to the patient and are placed remotely from the active electrode to carry the current back to the generator.

The return electrodes usually have a large patient contact surface area to minimize heating at the tissue site. A larger contact surface area results in lower localized heat intensity. Return electrodes are typically sized based on assumptions of the maximum current utilized during a particular surgical procedure and the duty cycle (i.e. the percentage of time the generator is on).

The first types of return electrodes were in the form of large metal plates covered with conductive jelly. Later, adhesive electrodes were developed with a single metal foil covered with conductive jelly or conductive adhesive. However, one issue with these adhesive electrodes was that if a portion of the electrode peeled from the patient, the contact area of the electrode with the patient decreased, thereby increasing the current density at the adhered portion and, in turn, increasing the heating at the tissue. This risked burning the patient in the area under the adhered portion of the return electrode if the tissue was heated beyond the point where circulation of blood could cool the skin.

To address this problem various return electrodes and hardware circuits, generically called Return Electrode Contact Quality Monitors (RECQMs), were developed. Such systems relied on placing multiple electrodes on the patient during electrosurgical procedures in order to dissipate the heat.

SUMMARY

The present disclosure relates to an electrosurgical return pad including a material backing configured to support first and second conductive materials. An insulative layer is placed between the first and second conductive materials, whereupon the first conductive material is oriented for contacting patient tissue. A switch element is mounted on the first conductive material and is activatable upon reaching a threshold condition, such as a threshold temperature. In one embodiment, the switch element includes a switch component formed from a shape-memory material.

The threshold condition may be a pre-determined temperature. At the threshold condition, the shape-memory alloy (e.g., Nitinol) transitions from an austenitic state to a martensitic state when a pre-determined temperature is reached. Thus, the switch element automatically activates, e.g., the shape-memory material mechanically deforms, to provide electrical continuity between the first and second conductive materials to offset the threshold condition. In another embodiment, a switch element includes a shape memory material that upon reaching the pre-determined temperature automatically provides electrical continuity between the first and second conductive materials by piercing the insulative layer disposed therebetween.

In one embodiment the switch element is electrically activated. In other embodiments, the switch element includes piezo-electric switches, piezo-electric sensors, impedance switches, temperature switches or combinations thereof.

The electrosurgical return pad may further include a conductive adhesive positioned between one of the conducive materials and the insulative layer and a border positioned on the periphery of the first and second conductive materials which supports a release liner thereon.

In still another embodiment, the switch element is positioned on a first conductive material and is adapted to communicate with an electrosurgical generator. A temperature sensor is coupled to the first conductive material and the electrosurgical generator. Upon reaching a pre-determined temperature, the temperature sensor communicates with the electrosurgical generator to activate the switch element, thus providing electrical continuity between the first and second conductive materials to offset the threshold condition.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

Figure 1:
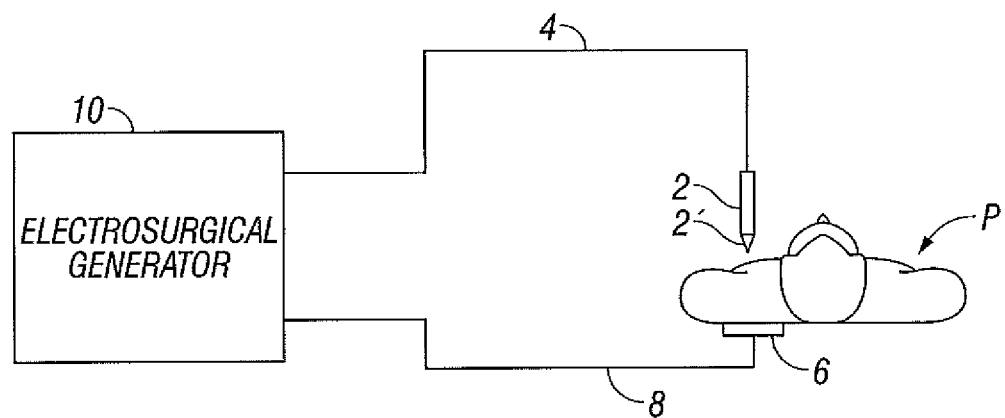
FIG. 1 is a schematic block diagram of an electrosurgical system according to the present disclosure.

FIG. 1 is a schematic illustration of an electrosurgical system 1 according to one embodiment of the present disclosure. System 1 includes an electrosurgical instrument 2 having one or more electrodes for treating tissue of a patient P. Instrument 2 is a monopolar instrument including one or more active electrodes (e.g., electrosurgical cutting probe, ablation electrode(s), etc.). Electrosurgical RF energy is supplied to instrument 2 by a generator 10 via an electrosurgical cable 4, which is connected to an active output terminal, allowing instrument 2 to coagulate, ablate and/or otherwise treat tissue. The energy is returned to generator 10 through a return electrode 6 via a return cable 8. The system may include one or more return electrodes 6 that are arranged to minimize the chances of tissue damage by maximizing the overall contact area with the patient P. In addition, generator 10 and return electrode 6 may be configured for monitoring so-called "tissue-to-patient" contact to insure that sufficient contact exists therebetween to further minimize chances of tissue damage.

Generator 10 includes input controls (e.g., buttons, activators, switches, touch screen, etc.) for controlling generator 10. In addition, generator 10 may include one or more display screens for providing the user with a variety of output information (e.g., intensity settings, treatment complete indicators, etc.). The controls allow the user to adjust power of the RF energy, waveform, and other parameters to achieve the desired waveform suitable for a particular task (e.g., coagulating, cutting, blending, etc.). Instrument 2 may also include a plurality of input controls that may be redundant with certain input controls of generator 10. Placing the input controls on the instrument 2 allows for easier and faster modification of RF energy parameters during a surgical procedure without requiring interaction with generator 10.

Figure 2:
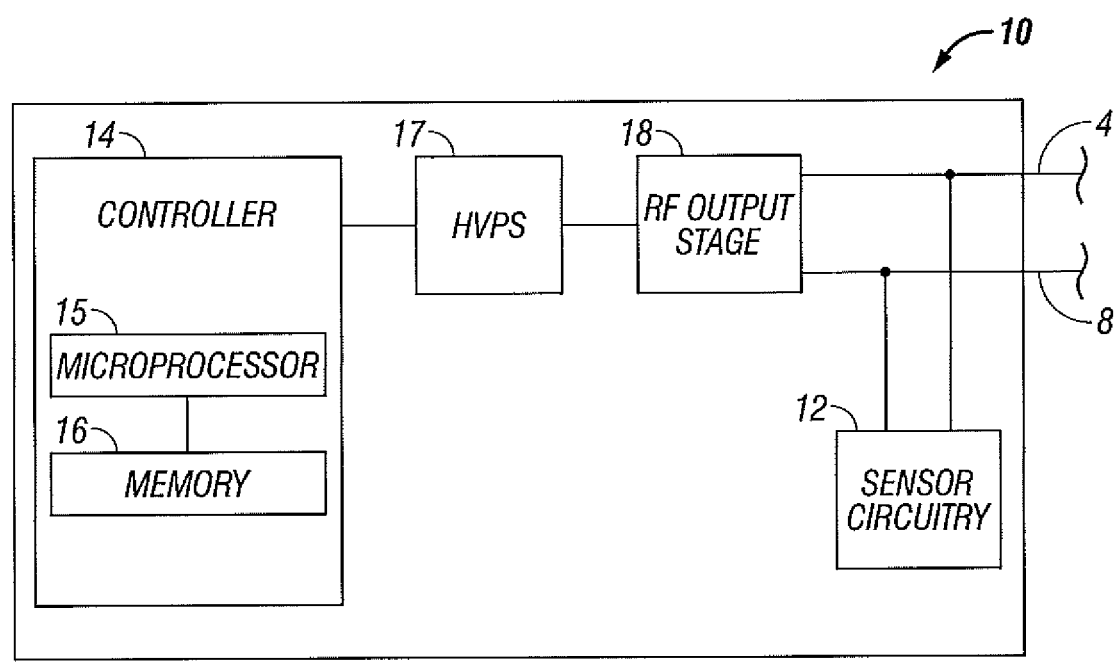
FIG. 2 is a schematic block diagram of the internal circuitry of a generator according to one embodiment of the present disclosure.

FIG. 2 shows a schematic block diagram of the generator 10 having a controller 14, a high voltage DC power supply 17 ("HVPS") and an RF output stage 18. HVPS 17 provides high voltage DC power to RF output stage 18, which, in turn, converts high voltage DC power into RF energy and delivers the RF energy to the active electrode. RF output stage 18 is configured to generate a plurality of sinusoidal waveforms having various duty cycles, peak voltages, crest factors, and other suitable parameters. Certain types of waveforms are suitable for specific electrosurgical modes and purposes. For instance, RF output stage 18 generates a 100% duty cycle sinusoidal waveform in cut mode, which is best suited for ablating, fusing and dissecting tissue, and a 1-25% duty cycle waveform in coagulation mode, which is best used for cauterizing tissue to stop bleeding.

Controller 14 includes a microprocessor 15 operably connected to a memory 16, which may be volatile type memory (e.g., RAM) and/or non-volatile type memory (e.g., flash media, disk media, etc.). Microprocessor 15 includes an output port that is operably connected to HVPS 27 and/or RF output stage 18 that allows microprocessor 15 to control the output of generator 10 according to either open and/or closed control loop schemes. Those skilled in the art will appreciate that microprocessor 15 may be substituted by any logic processor (e.g., control circuit) adapted to perform the calculations discussed herein.

A sensor circuit 12, includes one or more sensors, which measure a variety of tissue and energy properties (e.g., tissue impedance, tissue temperature, output current and/or voltage, etc.) and provide feedback to controller 14. Such sensors are within the purview of those skilled in the art. Controller 14 then signals the HVPS 17 and/or the RE output stage 18, which then adjusts DC and/or RE power supply, respectively. Controller 14 also receives input signals from the input controls of the generator 10 or the instrument 2. Controller 14 utilizes the input signals to adjust power outputted by generator 10 and/or performs other control functions thereon.

Figure 3:
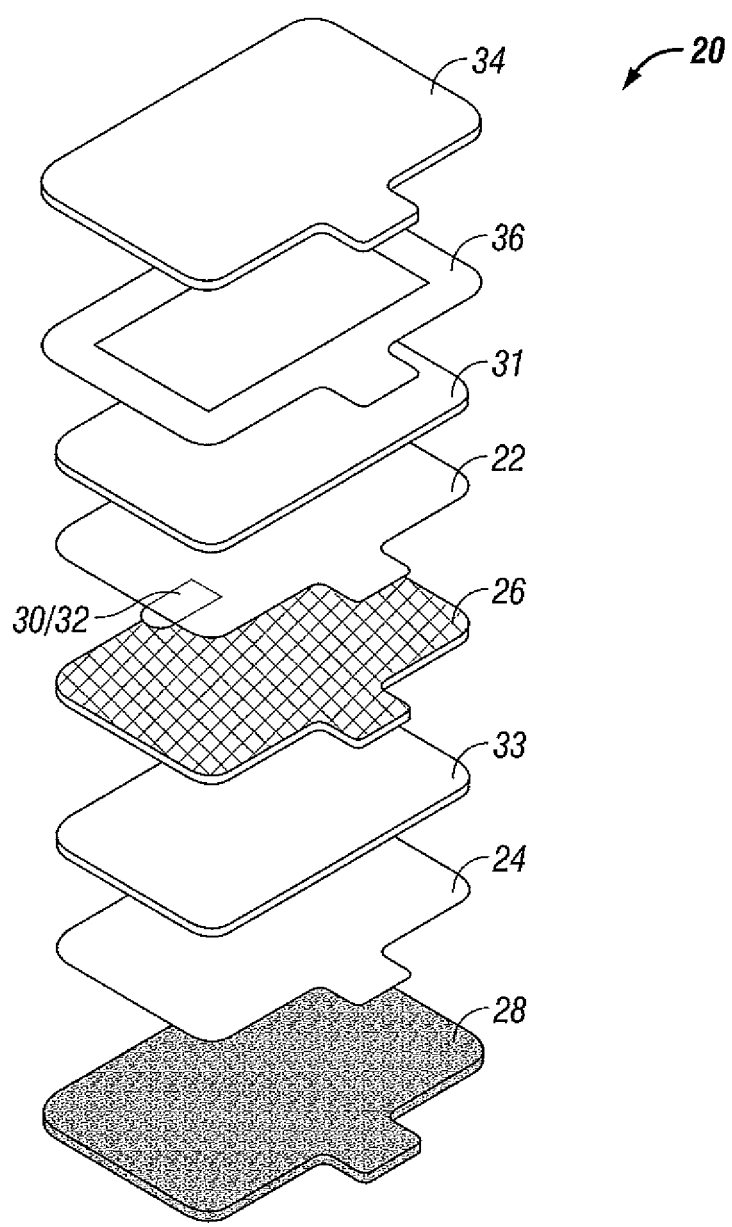
FIG. 3 is a perspective, exploded view of a return electrode pad according to the present disclosure.
Figure 4:
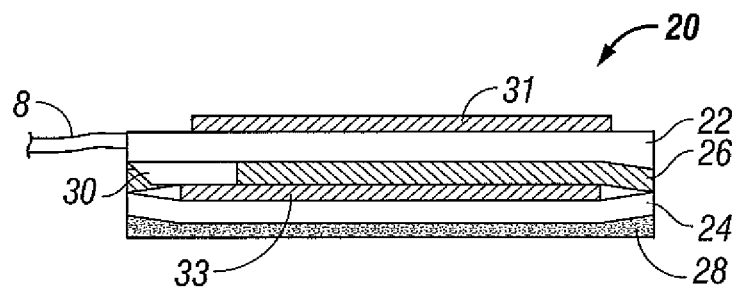
FIG. 4 is a cross-sectional view of the return electrode pad including first and second conductive materials and a switch element disposed therebetween, the switch element being shown in a first position.
Figure 5:
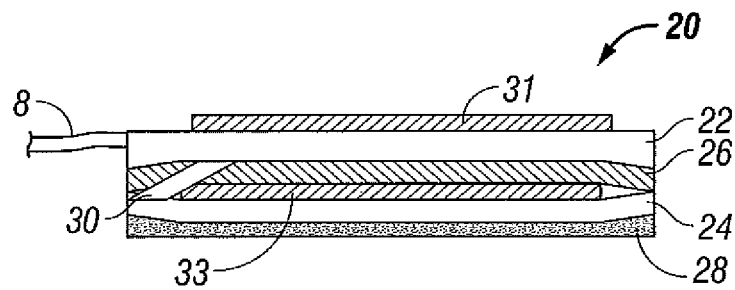
FIG. 5 is a cross-sectional view of the return electrode pad of FIG. 4 showing the switch element in a second position.

As depicted in FIGS. 3-5, the present disclosure relates to an electrosurgical return pad 20, which include a backing material 28 configured to support first and second conductive materials, 22 and 24, respectively. Backing material 28 is configured to protect/insulate the patient from any electrical current being absorbed by the return pad 20. Backing material 28 may be constructed from a polyethylene foam or any other suitable dielectric material known in the art. First and second conductive materials 22 and 24 may be constructed from a metal foil or any other suitable conductive material known in the art. As shown in FIG. 3, the first conductive material 22 is configured and oriented to contact a patient's skin to absorb electrical current from the active electrode 2' of an electrosurgical instrument 2 (see FIG. 1). The electrical energy is then returned to generator 10 through return electrode pad 6 via return cable 8, as previously discussed above.

In one embodiment, a second conductive material 24 is provided to facilitate the dissipation of energy or heat, if needed. Second conductive material 24 may be configured and dimensioned to be within electrode pad 20, thus reducing or eliminating placement of a plurality of electrode pads on a patient.

An insulative or dielectric layer 26 is configured and dimensioned to be disposed between first and second conductive materials 22 and 24 in order to prevent electrical communication during normal and/or initial surgical procedures. Insulative layer 26 separates first and second conductive materials 22 and 24 from each other by a predetermined distance (e.g., thickness of the insulative layer 26) thereby isolating first and second conductive materials 22 and 24 and reducing the overall conductivity of return electrode pad 20.

Electrosurgical return pad 20 further includes conductive adhesive layers 31 and 33 positioned on conducive materials 22 and 24. Adhesive layers 31 and 33 may include a Z-axis adhesive, a water-insoluble, hydrophilic, pressure-sensitive adhesive, or any combinations thereof, such as POLYHESIVE™ adhesive manufactured by Valleylab of Boulder, Colo. The adhesive may be conductive or dielectric. In particular, conductive adhesive layers 31 ensures an optimal surface contact area between electrosurgical return electrode pad 6 and the patient "P," which limits the possibility of a patient burn.

As shown in FIG. 3, a border adhesive 36 is positioned on the periphery of first and second conductive materials, 22 and 26, which supports a release liner 34 thereon. Border adhesive 36 may be acrylic adhesive reinforced with thermoplastic film or any other suitable material known in the art. Release liner 31 is provided to facilitate securement of conductive adhesive layer 31 and border adhesive 35 on electrode pad 20. Release liner 31 may also act as a dielectric or insulative barrier during pre-electrosurgical preparation. When a user desires to place electrode pad 20 on a patient, release liner may be easily removed to expose the first conductive material 22 along with adhesive layer 31 and border adhesive 35.

FIGS. 3-5 illustrate switch element 30 operatively associated with the first conductive material 22 to provide electrical continuity between the first and second conductive material 22 and 24. Switch element 30 contains a switch component 32, which automatically activates upon reaching a threshold condition "T", for example, a threshold temperature.

During use, if the overall current density of the pad increases and a heating condition occurs, the second conductive material is automatically added to the energy conducting path to offset or offload a portion of the current density. More particularly, engagement of first and second conductive material 22 and 24 occurs when a threshold condition "T" is reached. Threshold condition "T" is reached, for example, when a temperature, an inductance, and/or an impedance change occurs. A switch element 30 is included and is configured as an electrical intermediary between the first and second conductive materials 22, 24. The switch element 30 is automatically positioned from a first position wherein the first conductive material 22 absorbs heat to a second position, which electro-operatively connects the first and second conductive materials 22, 24. The switching element 30 may be automatically positioned by any electrical and/or mechanical devices, as explained in more detail below.

In one embodiment, switch component 32 may be a shape memory alloy ("SMA") made from nickel and titanium (e.g., Nitonol, FLEXINOL™, and MUSCLE WIRE™). SMAs change conformation (e.g., shape) at predetermined temperature conditions. The temperature at which the shape memory material reverts to its conformation is controlled by varying the ratio of the alloys in the SMA. The SMA of switch component 32 is configured to change shape at or around a maximum safe temperature, which may be from about 40° C. to about 45° C.

More particularly, SMAs are a family of alloys having anthropomorphic qualities of memory and trainability. SMAs have been applied to items such as actuators for control systems, steerable catheters and clamps. One of the most common SMAs is Nitinol, which can retain shape memories for two different physical configurations and changes shape as a function of temperature. Recently, other SMAs have been developed based on copper, zinc and aluminum and have similar shape memory retaining features.

SMAs undergo a solid state phase transition upon applied temperature and/or stress variations. A particularly useful attribute of SMAs is that after it is deformed by temperature/stress, it can completely recover its original shape on being returned to the original temperature. The ability of an alloy to possess shape memory is a result of the fact that the alloy undergoes a reversible transformation from an austenite phase to a martensite phase with a change in temperature/stress. Upon a change in temperature, the SMA of switch component 32 transitions from an austenite phase to a martensite phase to actuate one or more of switch elements 30.

Threshold condition "T" is at a predetermined temperature, for example, a temperature where a certain impedance and/or inductance occurs. At threshold condition "T", the shape-memory alloy (e.g., nitinol or flexinol) transitions from an austenite phase to a martensite phase when a pre-determined temperature is reached. Thus, switch element 30 automatically activates, i.e., the SMA mechanically deforms, to provide electrical continuity between first and second conductive materials, 22 and 24, by piercing insulative layer 26 disposed therebetween to offset threshold condition "T".

As shown in the comparison of FIGS. 4 and 5, switch component 30, which is disposed on first conductive material 22, changes shape and pierces insulative layer 26 to contact second conductive material 24. Switch component 30 provides electrical continuity, e.g., a conducting bridge, between the first and second conductive materials 22 and 24. A plurality of switch components 30 may be disposed on first conductive material 22 and pierce the layer 26 in sequence (or simultaneously) to offset the current density and heat build-up.

In another embodiment, switch element 30 may be electrically activated by generator 10. For example, switch element 30 may include a different type of switch component 32, such as a piezo-electric switch, piezo-electric sensor, impedance switch, temperature switch or combinations thereof.

Figure 6:
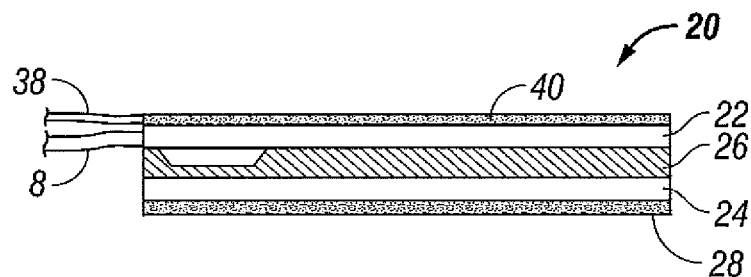
FIG. 6 is a cross-sectional view of the return electrode pad including first and second conductive materials and a temperature sensor disposed therebetween.

In yet another embodiment, switch element 30 is positioned on a first conductive material 22 and is adapted to communicate with electrosurgical generator 10 via a temperature sensor 40. As depicted in FIG. 6, temperature sensor 40 is coupled to first conductive material 22 and electrosurgical generator 10. Temperature sensor 40 communicates with generator 10 via interrogation cable 38. Interrogation cable 38 may send and receive communication signals between generator 10 and electrode pad 20 for different parameters. For example, upon reaching a pre-determined temperature threshold, temperature sensor 40 communicates with electrosurgical generator 10 to activate switch element 30, thus providing electrical continuity between the first and second conductive materials, 22 and 24, to offset heat build-up.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical return pad, comprising:
   a material backing configured to support an insulative layer having a top side and a bottom side opposing the top side, a first conductive material disposed on the top side of the insulative layer, and a second conductive material disposed on the bottom side of the insulative layer, at least the first conductive material oriented for contacting patient tissue; and
   at least one switch element disposed on at least the first conductive material and activatable upon reaching a threshold condition;
   wherein upon reaching the threshold condition, the at least one switch element automatically activates to provide electrical continuity between the first and second conductive materials to offset the threshold condition,
   wherein the switch element includes at least one switch component formed from a shape-memory material.

2. An electrosurgical return pad according to claim 1, wherein the threshold condition is a pre-determined temperature and the shape-memory material transitions from an austenitic state to a martensitic state upon reaching the pre-determined temperature to automatically activate the at least one switch component of the at least one switch element to provide electrical continuity between the first and second conductive materials.

3. An electrosurgical return pad according to claim 1, wherein the shape memory material includes an alloy selected from the group consisting of nitinol and flexinol.

4. An electrosurgical return pad according to claim 1, wherein the switch element mechanically deforms to provide electrical continuity between the first and second conductive materials.

5. An electrosurgical return pad according to claim 1, wherein the switch element is selected from the group consisting of piezo-electric switches, piezo-electric sensors, impedance switches and temperature switches.

6. An electrosurgical return pad according to claim 1, wherein the return pad further includes:
   at least one conductive adhesive disposed between one of the first and second conducive materials and the insulative layer.

7. An electrosurgical return pad according to claim 1, wherein the return pad further includes:
   a border disposed about the periphery of at least one of the first and second conductive materials which supports a release liner thereon.

8. An electrosurgical return pad according to claim 1, wherein the threshold condition is a pre-determined temperature.

9. An electrosurgical return pad, comprising:
   a material backing configured to support an insulative layer having a top side and a bottom side opposing the top side, a first conductive material disposed on the top side of the insulative layer, and a second conductive material disposed on the bottom side of the insulative layer, at least the first conductive material oriented for contacting patient tissue; and
   a switch element disposed on at least the first conductive material and activatable upon reaching a predetermined temperature, the switch element including a shape memory material that deforms from an austenitic state to a martensitic state upon reaching the pre-determined temperature to automatically provide electrical continuity between the first and second conductive materials by piercing the insulative layer disposed therebetween.

10. An electrosurgical return pad according to claim 9, wherein the threshold condition is a pre-determined temperature.

11. An electrosurgical return pad, comprising:
   a material backing configured to support an insulative layer having a top side and a bottom side opposing the top side, a first conductive material disposed on the top side of the insulative layer, and a second conductive material disposed on the bottom side of the insulative layer, at least the first conductive material oriented for contacting patient tissue;
   at least one switch element disposed on at least the first conductive material and adapted to communicate with an electrosurgical generator; and
   at least one temperature sensor operably coupled to at least the first conductive material, the temperature sensor being adapted to communicate with the electrosurgical generator;
   wherein upon reaching a pre-determined temperature, the temperature sensor communicates with the electrosurgical generator to activate the switch element to provide electrical continuity between the first and second conductive material to offset the threshold condition.

* * * * *